United States Patent
Enevoldsen et al.

(10) Patent No.: US 8,037,748 B2
(45) Date of Patent: Oct. 18, 2011

(54) METHOD FOR ALIGNING A COMPONENT INTO A WIND DIRECTION AND SENSOR FOR DETERMINING MISALIGNMENT OF A COMPONENT RELATIVE TO A WIND DIRECTION

(75) Inventors: Peder Bay Enevoldsen, Vejle (DK); Ib Frydendal, Føvling (DK); Steffen Frydendal Poulsen, Silkeborg (DK); Rune Rubak, Silkeborg (DK)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 12/560,524

(22) Filed: Sep. 16, 2009

(65) Prior Publication Data

US 2010/0064796 A1    Mar. 18, 2010

(30) Foreign Application Priority Data

Sep. 17, 2008   (EP) .................................... 08016398

(51) Int. Cl.
*G01W 1/00*    (2006.01)

(52) U.S. Cl. .................................................... 73/170.01
(58) Field of Classification Search ........................ None
See application file for complete search history.

(56) References Cited

U.S. PATENT DOCUMENTS

| 4,298,313 | A | 11/1981 | Hohenemser et al. | |
|---|---|---|---|---|
| 6,526,821 | B1 | 3/2003 | Corda et al. | |
| 2006/0220389 | A1* | 10/2006 | Shibata et al. | 290/55 |
| 2007/0125165 | A1* | 6/2007 | Ormel et al. | 73/170.01 |
| 2010/0102559 | A1* | 4/2010 | Enevoldsen et al. | 290/44 |

FOREIGN PATENT DOCUMENTS

| EP | 0083819 A1 | 2/1983 |
|---|---|---|
| EP | 1505299 A1 | 2/2005 |
| JP | 2002116220 A | 4/2002 |

* cited by examiner

*Primary Examiner* — Andre Allen

(57) ABSTRACT

In one aspect, a method for aligning a component into a wind direction is provided. The component comprises a sensor which is located such that at least part of the sensor is exposed to the wind. A signal is measured based on the force acting on the sensor due to the wind, and the component is rotated depending on the measured signal. Additionally a sensor for determining misalignment of a component relative to a wind direction is provided. The sensor comprises at least one flat element and at least one tool or device for measuring the force acting on the flat element.

15 Claims, 3 Drawing Sheets

METHOD FOR ALIGNING A COMPONENT INTO A WIND DIRECTION AND SENSOR FOR DETERMINING MISALIGNMENT OF A COMPONENT RELATIVE TO A WIND DIRECTION

CROSS REFERENCE TO RELATED APPLICATIONS

This application claims priority of European Patent Office application No. 08016398.3 EP filed Sep. 17, 2008, which is incorporated by reference herein in its entirety.

FIELD OF INVENTION

The present invention relates to a method for aligning a component into a wind direction and to a sensor for determining misalignment of a component relative to a wind direction. The present invention further relates to a wind turbine.

BACKGROUND OF INVENTION

The alignment of, for example, horizontal axis wind turbines into a particular wind direction is crucial in order to avoid high structural loads and in order to produce optimal power. The wind direction is typically measured by use of a wind vane or by use of a sonic wind sensor.

SUMMARY OF INVENTION

It is an objective of the present invention to provide an advantageous method for aligning a component into a wind direction. It is a second objective of the present invention to provide an advantageous sensor for determining misalignment of a component relative to a wind direction. A third objective of the present invention is to provide an advantageous wind turbine.

The first objective is solved by a method for aligning a component into a wind direction. The second objective is solved by a sensor for determining misalignment of a component relative to a wind direction. The third objective is solved by a wind turbine. The dependent claims define further developments of the invention.

The inventive method for aligning a component into a wind direction is related to a component which comprises a sensor. The sensor is located such that at least part of the sensor is exposed to the wind. The inventive method comprises the steps of measuring a signal depending on the force acting on the sensor due to the wind and rotating the component depending on the measured signal. An advantage of the inventive method is that the measurement can be performed on fixed components. The method does not provide a measurement of the wind direction in degrees, the method is rather designed to detect misalignment. This eliminates flutter instability and provides a robust sensor. With robust detection of misalignment a better alignment is provided and an increase in structural loads due to a misalignment is avoided. In addition, power production losses due to misalignment are avoided.

Advantageously the measured signal can be integrated over time periods. This provides a robust determination of the yaw misalignment.

Generally the force, the strain, the torque or the bending moment acting on at least part of the sensor can be measured. For example, the measurement can be performed by means of a force gauge. The force gauge may comprise, for instance, a spring. Another example is to use a strain gauge measuring the strain of one or more elements, where the measured strain corresponds to the force acting on the elements.

Preferably the sensor may comprise a flat element. The flat element can comprise two sides. The signal can be measured on one or on both sides of the flat element. The flat element may especially comprise a plate or a symmetric aerodynamic profile. The symmetric aerodynamic profile may, for example, be a vane.

Preferably the component is rotated such that norm of the measured signal is extremal, for example minimal or maximal. If, for instance, the normal of the surface of the used flat element is orientated parallel to the wind direction when the component is aligned, then the norm of the measured signal is minimal. Alternatively, if the normal of the surface of the used flat element is orientated perpendicular to the wind direction when the component is aligned, then the norm of the measured signal is maximal.

Moreover, the sensor can be calibrated by rotating the sensor and/or the flat element relatively to a rotation axis of the component. The calibration can preferably be performed before measuring the signal depending on the force acting on the sensor.

Furthermore, the sensor can comprise a centreline which is orientated perpendicular to a rotation axis of the component. The sensor can further comprise a first flat element and a second flat element. The first flat element and the second flat element can be positioned at a distance from each other. Moreover, the first flat element and the second flat element can be positioned such that the first flat element includes an angle of $+\alpha$ with the centreline and the second flat element includes an angle $-\alpha$ with the centreline. The angle $\alpha$ may be the accepted misalignment angle for the component. In this case the component may be rotated only if on both flat elements a force of the same algebraic sign along an axis perpendicular to the centerline and perpendicular to rotation axis of the component is measured.

The component can be part of a wind turbine, especially part of a horizontal axis wind turbine.

Generally, the bending moment may be provided by measuring the strain on only one side of the flat element. The forces on the flat element, for example on the flat plate or the symmetric aerodynamic profile, may be measured with other sensors or tools than spring sensors. The rotation of the sensor may be adjustable in order to provide for calibrating of the sensor. The location of the sensor is preferable on top of a nacelle of a wind turbine, but it may be placed on other the places on the nacelle. The flat element, especially the sensor plates or profiles may be of any appropriate size. Moreover, if the sensor is designed with two flat elements the distance between these elements may be of any appropriate distance.

The inventive sensor for determining misalignment of a component relative to a wind direction comprise at least one flat element and at least one tool or device for measuring the force acting on the flat element. The flat element may especially comprise a plate or a symmetric aerodynamic profile. The symmetric aerodynamic profile can be a vane, for example.

Advantageously the position of the sensor relative to the component may be adjustable. For example, the sensor may be rotatable in order to provide for calibrating of the sensor.

Moreover, the sensor can comprise a centerline which is orientated perpendicular to a rotation axis of the component. The sensor can further comprise a first flat element and a second flat element. The first flat element and the second flat element can be positioned at a distance from each other. Furthermore, they can be positioned such that the first flat element includes angle of $+\alpha$ with the centerline and the second flat element includes angle of −α with the centerline. The angle α may be the excepted misalignment angle for the component, for example for the wind turbine. In this case a yaw actuator can be activated only if the forces or moments about the supporting edge between the flat elements and a mounting element are both positive or both negative, which means a moment in the same direction.

The inventive wind turbine comprises at least one inventive sensor as previously described. The inventive wind turbine may especially comprise a nacelle and the sensor may be located on top of the nacelle. The nacelle may comprise a centerline which is orientated parallel to the rotation axis of the wind turbine. The sensor can be located at the centerline on top of the nacelle. Alternatively, the sensor can be located at a particular distance from the centerline. Preferably the inventive wind turbine comprises a yaw actuator. By means of the yaw actuator the nacelle and the rotor of the wind turbine can be rotated along the vertical axis of the wind turbine.

The present invention provides a method and a sensor to detect misalignment of a component relative to a wind direction. The measurement of forces on fixed components provides a robust detection of misalignments. This allows for a better alignment and an increase in structural loads due to misalignment is avoided. In addition, power production losses, for example of wind turbines, due to a misalignment are avoided.

BRIEF DESCRIPTION OF THE DRAWINGS

Further features, properties and advantages of the present invention will become clear from the following description of embodiments in conjunction with accompanying drawings. The described features are advantageous alone and in combination with each other.

DETAILED DESCRIPTION OF INVENTION

Figure 1:
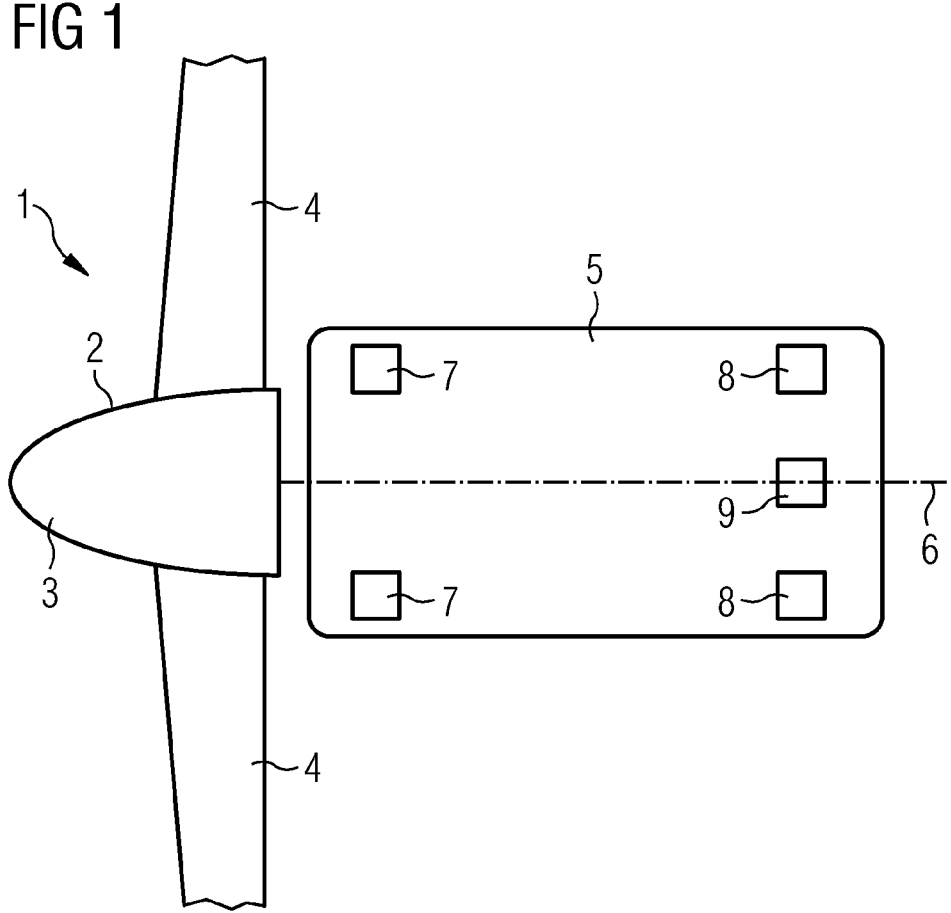
FIG. 1 schematically shows a part of a wind turbine in a top view.

A first embodiment of the present invention will now be described with reference to FIGS. 1 to 3. FIG. 1 schematically shows part of a wind turbine 1 in a top view. The wind turbine 1 comprises a rotor 2 and a nacelle 5. The rotor 2 is mounted on the nacelle 5 and comprises a hub 3 and a number of wind turbine rotor blades 4. The wind turbine rotor blades 4 are connected to the hub 3.

On top of the nacelle 5 at least one sensor 7, 8, 9 is located. Examples for different locations of the sensor on top of the nacelle 5 are indicated by the reference numerals 7, 8 and 9. The nacelle 5 comprises a centerline 6. The sensor 9 is situated at the centerline 6. Furthermore, it is possible to position the sensor at a particular distance from the centerline 6. This is shown for the sensors 7 and 8. The sensors 7 are positioned close to the rotor 2. The sensors 8, as well as the sensor 9, are positioned at a nearly maximal distance from the rotor 2. Positioning the sensor 8, 9 as far as possible away from the rotor 2 reduces the influence of turbulences caused by the rotor 2 on the measurement.

Figure 2:
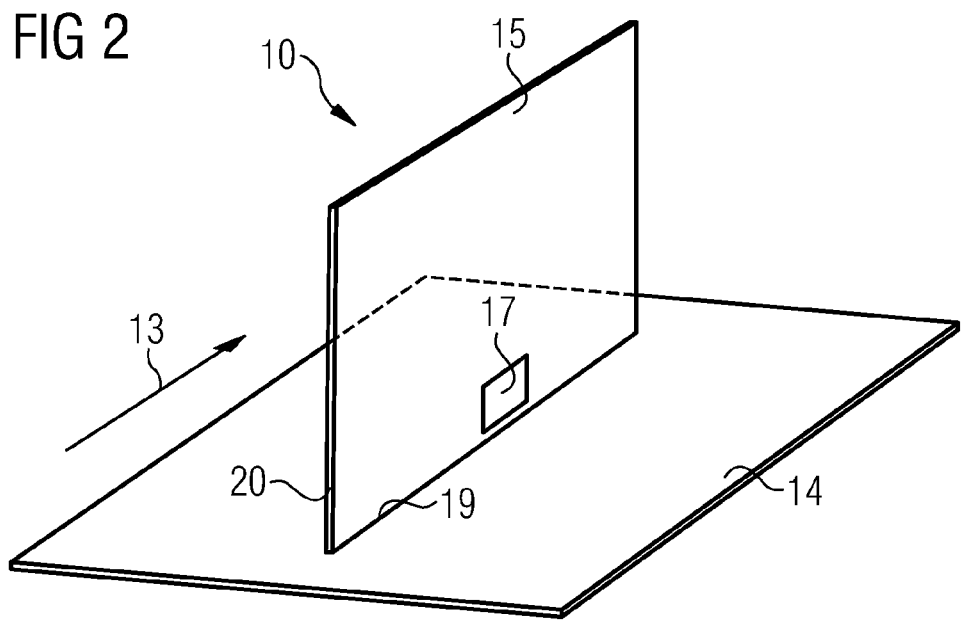
FIG. 2 schematically shows an inventive sensor in a perspective view.

FIG. 2 schematically shows a sensor 10 in a perspective view. The sensor 10 comprises a mounting plate 14, a flat plate 15 and a tool or device for measuring force 17. The flat plate 15 comprises a horizontal edge 19 and a vertical edge 20. It is connected to the mounting plate 14 at its horizontal edge 19, which has the function of a supporting edge. The tool or device for measuring force 17 is located at one side of the flat plate 15 close to the mounting plate 14, which means close to the supporting edge.

The sensor 10 is positioned on top of the nacelle 5 of the wind turbine 1. It is positioned such that if the rotor 2 of the wind turbine 1 is aligned into the wind direction 13, then the wind direction 13 is parallel to the surface of the flat plate 15, which means parallel to the supporting edge 19. If the rotor 2 is not aligned to wind direction 13, the wind causes force acting on one of the surfaces of the flat plate 15. This force and/or the caused strain and/or the caused bending moment and/or the caused torque are measured by means of the tool or device for measuring force 17.

After measuring a signal depending on the force acting on the flat plate 15 due to the wind the nacelle 5 can be rotated about the vertical axis of the wind turbine 1 depending on the measured signal, if necessary. Preferably the nacelle 5 is rotated until the measured signal, especially the measured force, is minimal. Generally, the pressure on the sides of the plate 15 situated in the wind 13 will be equal only if the plate 15 is aligned in the wind direction 13. A measurement of the strain on one or both sides of the plate 15 provides for a measurement of the bending moment in the flat plate 15. Advantageously the signal is integrated over time periods for robust determination of the yaw misalignment.

Alternatively the sensor 10 can be positioned on the nacelle 5 such that in the aligned state of the rotor 2 the wind direction 13 is orientated perpendicular to one of the surfaces of the flat plate 15. In this case, for aligning the rotor 2 the nacelle has to be rotated until the measured signal, especially the measured force, is maximal.

Figure 3:
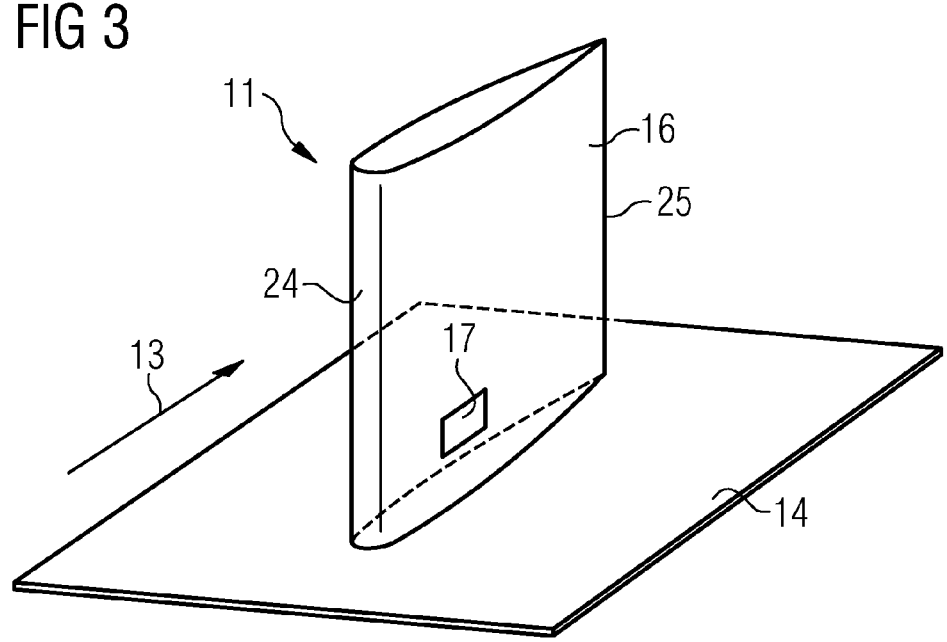
FIG. 3 schematically shows another variant of an inventive sensor in perspective view.

A further alternative for an inventive sensor is shown in FIG. 3. FIG. 3 schematically shows an inventive sensor 11 in a perspective view. Instead of a flat plate 15 in FIG. 2, the inventive sensor 11 which is shown in FIG. 3 comprises a symmetric aerodynamic profile which is designed as vane 16. The vane 16 comprises a leading edge 24 and a trailing edge 25. It is connected to the mounting plate 14 such that the leading edge 24 and the trailing edge 25 are perpendicular to the surface of the mounting plate 14. A tool or device for measuring force 17 is positioned on the surface of the vane 16 close to the mounting plate 14.

Generally it is advantageous to position the tool or device for measuring force 17 close to the mounting plate 14 because the force due to the wind is higher close to the mounting plate than away from the mounting plate 14.

The inventive sensor 11 is preferably mounted on top of the nacelle 5 of the wind turbine 1 such that in the aligned case the wind 13 arrives at the vane 16 at its leading edge 24 and leaves it at its trailing edge 25.

A second embodiment of the present invention will now be described with reference to FIGS. 1 and 4. Elements corresponding to elements of the first embodiment will be designated with the same reference numerals and will not be described again in detail.

Figure 4:
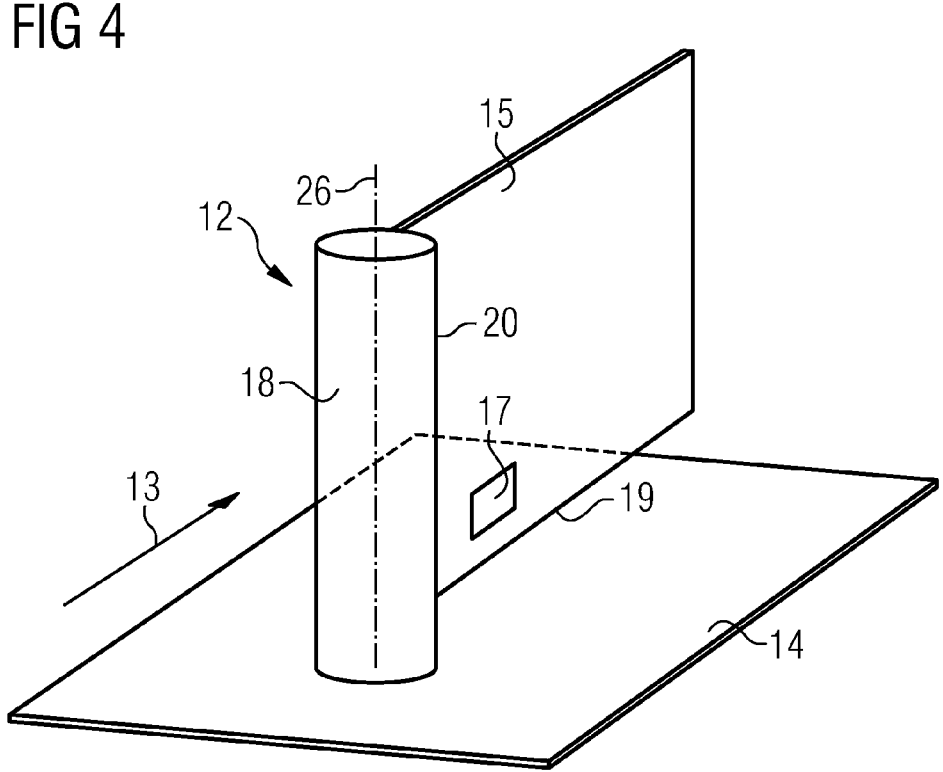
FIG. 4 schematically shows a further variant of an inventive sensor in a perspective view.

FIG. 4 schematically shows an inventive sensor 12 in a perspective view. The sensor 12 comprises a mounting plate 14, a mounting element 18, a flat plate 15 and a tool or device for measuring force 17. The mounting element 18 has the shape of a cylinder, a rod or a pillar. The mounting element 18 comprises a centerline 26 in its longitudinal direction. The mounting element 18 is connected to the mounting plate 14 such that the centerline 26 is perpendicular to the surface of the mounting plate 14.

The flat plate 15 is connected to the mounting element 18 such that the vertical edge 20 of the flat plate 15 runs parallel to the centerline 26 of the mounting element 18 and the horizontal edge 19 of the flat plate 15 runs parallel to the surface of the mounting plate 14. The flat plate 15 comprises a tool or device for measuring force 17 which is preferably located close to the mounting element 18. In the present embodiment the vertical edge 20 of the flat plate 15 acts as supporting edge.

The sensor 12 is preferably mounted on top of the nacelle 5 such that in the aligned case wind direction 13 runs parallel to the surface of the flat plate 15 which means parallel to the horizontal edge 19. Advantageously, in the aligned case the wind arrives at the sensor 12 at the mounting element 18 and leaves it at the flat plate 15. Generally, the mounting element 18 provides a support of the flat plate 15 at the upwind edge.

A third embodiment of the present invention will now be described with reference to FIGS. 1, 5 and 6. Elements corresponding to elements of the first and the second embodiment will be designated with the same reference numerals and will not be described again in detail.

Figure 5:
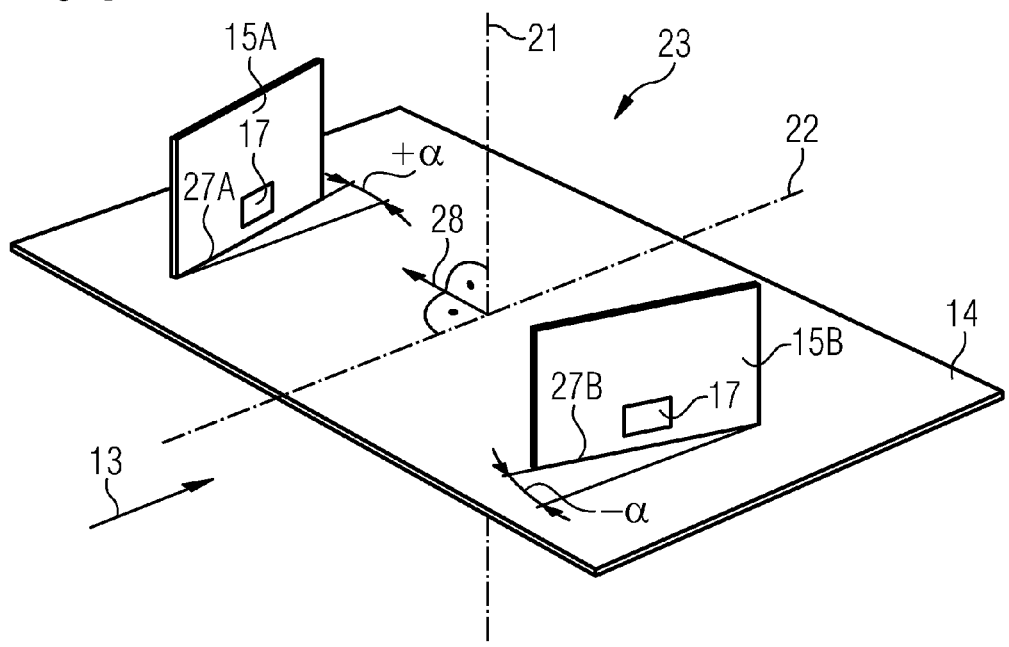
FIG. 5 schematically shows an inventive sensor comprising two flat elements in a perspective view.

FIG. 5 schematically shows an inventive sensor 23 in a perspective view. The sensor 23 is preferably mounted on top of the nacelle 5 of the wind turbine 1. The rotation axis of the wind turbine 1 is indicated by reference numeral 21 in FIG. 5. The sensor 23 comprises a mounting plate 14, two flat plates 15a, 15b and centerline 22. The centreline 22 runs perpendicular to the rotation axis 21 of the wind turbine 1. The flat plates 15a and 15b are mounted onto the mounting plate 14 as described in the first embodiment. They are equipped each with at least one tool or device for measuring force 17 as described in the first embodiment. Instead of flat plates 15a and 15b also vanes 16, as described in the first embodiment, can be used.

The flat plates 15a and 15b are positioned at a particular distance from each other. The distance between the two plates 15a, 15b is preferably large enough for the plates 15a, 15b to not have any flow interaction. The two plates 15a, 15b have been rotated about +/- the angle α relative to parallel, which means that the flat plate 15a includes an angle of +α with the centerline 22 and the flat plate 15b includes an angle of −α with the centerline 22. The angle α is the excepted misalignment angle for the turbine 1. Hence the rotor 2 of the turbine 1 should be activated only if the force or moment about the supporting edges 27a, 27b where the flat plates 15a, 15b are connected to the mounting plate 14 are both positive or negative relative along an axis 28 which runs perpendicular to the rotation axis 21 of the wind turbine 1 and perpendicular to the centreline 22 of the sensor 23. In this case the measured force or moment has the same direction. In other words, the rotor 2 is rotated only if on both flat elements a force or moment of the same algebraic sign along the axis 28 perpendicular to the centreline 22 and perpendicular to vertical rotation axis 21 of the wind turbine is measured. The rotor 2 can be rotated along the vertical rotation axis 21 of the wind turbine 1 by means of a yaw actuator.

Figure 6:
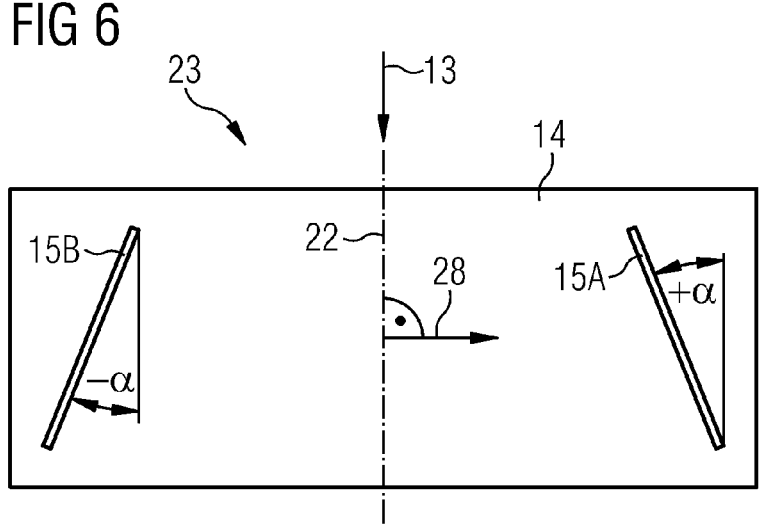
FIG. 6 schematically shows the inventive sensor which is shown in FIG. 5 in a top view.

FIG. 6 schematically shows the inventive sensor 23 which is shown in FIG. 5 in a top view. FIGS. 5 and 6 show the sensor 23 in the aligned case, where the wind direction 13 runs parallel to the centerline 22.

Generally the inventive sensor 7, 8, 9, 10, 11, 12, 23, in all embodiments can comprise at least one flat element 15, 15a, 15b, 16, each equipped with at least one tool or device for measuring force 17. Preferably each side of the flat element 15, 15a, 15b, 16, is equipped with at least one tool or device for measuring force 17. The tool or device 17 is typically a strain gauge measuring the strain of a plate. This measured strain corresponds to the wind forces acting on the plate.

The invention claimed is:

1. A method for aligning a component into a wind direction, comprising:
    providing a sensor arranged on the component so that at least part of the sensor is exposed to the wind;
    measuring a signal based on a force acting on the sensor due to the wind, the measuring in order to detect a misalignment of the component; and
    rotating the component based on the measured signal in order to improve the alignment of the component.

2. The method as claimed in claim 1, further comprises repeating the measuring and the rotating over a time period.

3. The method as claimed in claim 1, wherein a force, a strain, a torque or the bending moment acting on at least part of the sensor is measured and the rotating is adjusted according to the measurement.

4. The method as claimed in claim 1, wherein the sensor comprises a flat element comprising two sides and the signal is measured on one or both sides of the flat element.

5. The method as claimed in claim 4, wherein the flat element comprises a plate or a symmetric aerodynamic profile.

6. The method as claimed in claim 1, rotating the component such that the norm of the measured signal is extremal.

7. The method as claimed in claim 4, further comprises calibrating the sensor by rotating the sensor or the flat element relatively to a rotation axis of the component.

8. The method as claimed in claim 4, further comprises calibrating the sensor by rotating the sensor and the flat element relatively to a rotation axis of the component.

9. The method as claimed in claim 1, wherein the sensor comprises:
    a centreline orientated perpendicular to a rotation axis of the component,
    a first flat element and a second flat element, the first flat element and the second flat element being positioned at a distance from each other so that the first flat element includes an angle +α with the centreline and the second flat element includes an angle −α with the centreline, and the rotating the component occurs only when on both flat elements a force of the same algebraic sign along an axis perpendicular to the centreline and perpendicular to the rotation axis of the component is measured.

10. The method as claimed in claim 1, wherein the component is part of a wind turbine.

11. A wind turbine, comprising:
    a component;
    a sensor arranged on the component so that at least part of the sensor is exposed to the wind, the sensor determines a misalignment of the component relative to a wind direction, the sensor comprising:
        a first flat element, and
        a first measuring instrument arranged on the first flat element and which measures the force acting on the first flat element in order to determine the misalignment, a rotational unit rotates the component based on the measured signal in order to improve the alignment of the component.

12. The wind turbine as claimed in claim 11, further comprises a nacelle with the sensor arranged on top of the nacelle.

13. The wind turbine as claimed in claim 11, wherein the first flat element comprises a plate or a symmetric aerodynamic profile.

14. The wind turbine as claimed in claim 11, wherein the position of the sensor relative to the component is adjustable.

15. The wind turbine as claimed in claim 11, wherein in the sensor comprises:

a centreline orientated perpendicular to a rotation axis of the component, a second flat element, the first flat element and the second flat element being positioned at a distance from each other so that the first flat element includes an angle $+\alpha$ with the centreline and the second flat element includes an angle $-\alpha$ with the centreline, and the rotating the component occurs only when on both flat elements a force of the same algebraic sign along an axis perpendicular to the centreline and perpendicular to the rotation axis of the component is measured.

\* \* \* \* \*